United States Patent
Brock-Fisher

(10) Patent No.: US 6,413,221 B1
(45) Date of Patent: Jul. 2, 2002

(54) ULTRASONIC SYSTEM AND METHOD EMPLOYING VARIABLE FILTERING OF ECHO RETURN SIGNALS

(76) Inventor: George A Brock-Fisher, 15 Webster St., Andover, MA (US) 01810

( * ) Notice: Subject to any disclaimer, the term of this patent is extended or adjusted under 35 U.S.C. 154(b) by 0 days.

(21) Appl. No.: 09/502,516

(22) Filed: Feb. 11, 2000

(51) Int. Cl.[7] .................................................. A61B 8/00
(52) U.S. Cl. ..................................................... 600/458
(58) Field of Search ................................ 600/437, 440, 600/441, 443, 447, 453–456, 458

(56) References Cited

U.S. PATENT DOCUMENTS

| | | |
|---|---|---|
| 5,410,516 A | 4/1995 | Uhlendorf et al. |
| 5,577,505 A | 11/1996 | Brock-Fisher et al. |
| 5,833,613 A | 11/1998 | Averkiou et al. |
| 5,879,303 A | 3/1999 | Averkiou et al. |
| 6,110,120 A * | 8/2000 | Holley et al. ............ 600/458 |

* cited by examiner

*Primary Examiner*—Francis J. Jaworski
(74) *Attorney, Agent, or Firm*—John Vodopia

(57) ABSTRACT

The method of the invention controls an ultrasound system to image a microbubble contrast agent in a region of fluid flow. A transducer is caused to transmit ultrasound signals and to receive echoes resulting from interaction of the ultrasound signals with both tissue and microbubbles. A transmitter enables the transducer to transmit the ultrasound signals at a plurality of power levels. A receiver selectively extracts signal components from the echo signals that fall within a determined bandwidth, and is controlled to alter the determined bandwidth (or the center frequency thereof) in accordance with which of the power levels is transmitted.

10 Claims, 2 Drawing Sheets

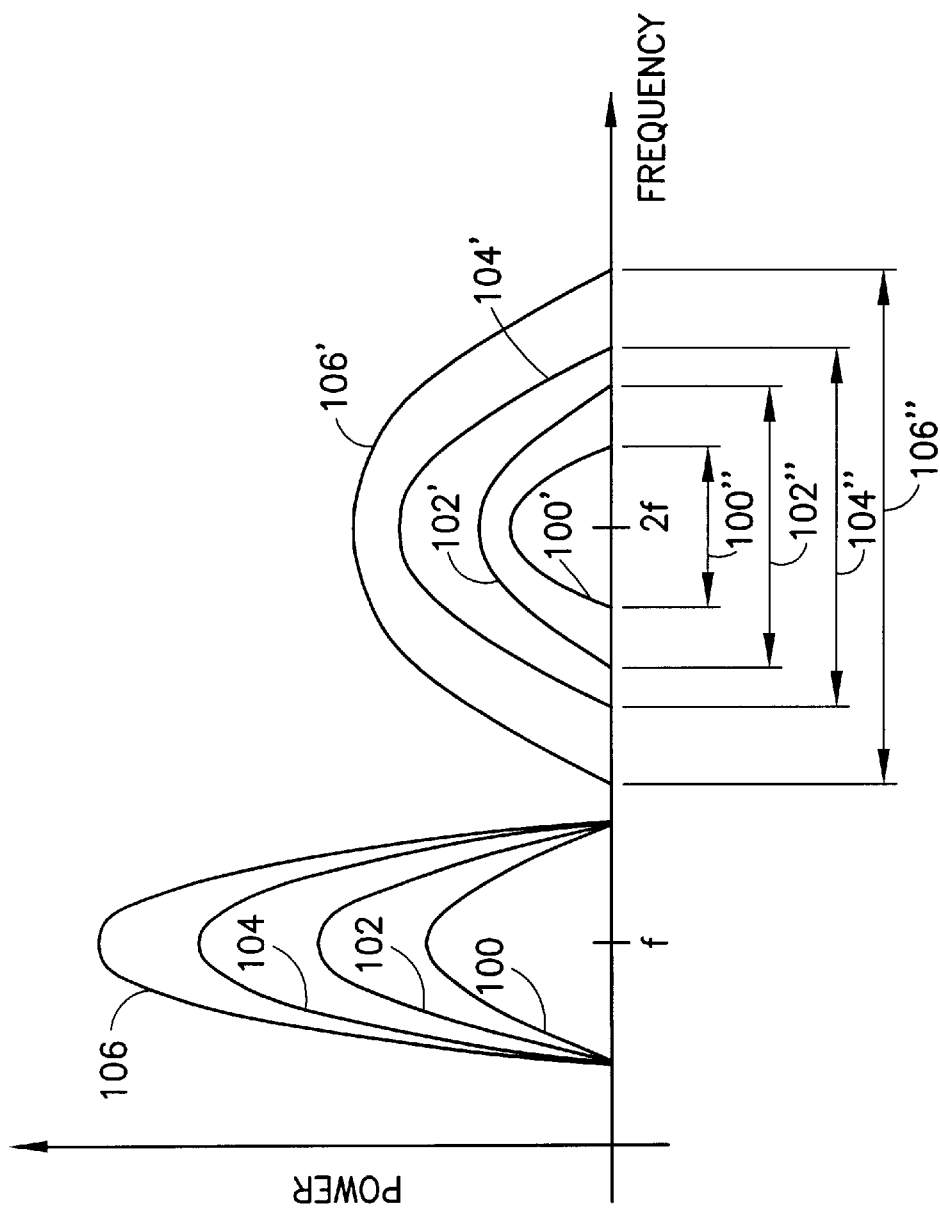

ULTRASONIC SYSTEM AND METHOD EMPLOYING VARIABLE FILTERING OF ECHO RETURN SIGNALS

FIELD OF THE INVENTION

This invention relates to ultrasonic imaging of perfusion of an anatomical region and, more particularly, to a method for enabling imaging of a contrast agent with reduced clutter.

BACKGROUND OF THE INVENTION

Current ultrasonic imaging systems make use of contrast agents in circulation to enhance ultrasound returns. Contrast agents are substances which strongly interact with ultrasound waves and return echoes which may be clearly distinguished from those returned by blood and tissue. Microbubbles are currently employed as a contrast agent and provide a non-linear behavior in certain acoustic fields. Such behavior is readily detectable by use of known algorithms. Microbubble contrast agents are useful for imaging of the body's vascular system and are injectable through the veins and arteries. They are subsequently filtered from the blood stream by the lungs, kidneys and liver.

Microbubble contrast agents generally comprise coated gas bubbles that are stable in the body for a significant period of time. The coating shells serve to protect the gas from diffusion into the blood stream. At moderately high ultrasound pressure amplitudes, the shells of the microbubbles can be caused to rupture, freeing the internal gas and substantially eliminating the detectability thereof by incident ultrasound waves.

U.S. Pat. No. 5,410,516 to Uhlendorf et al. describes an ultrasound system that produces images from echo returns from a microbubble contrast agent. The echo signals that are used for imaging are those that exhibit harmonic and sub-harmonic relationships to the fundamental transmission frequency.

U.S. Pat. No. 5,833,613 to Averkiou et al. discloses an ultrasound method for imaging of contrast agents. In one embodiment, a rate of re-perfusion of an anatomical region is accomplished by initially destroying the contrast agent within the region, and then subsequently imaging the region to determine the rate of re-insertion of the contrast agent. The Averkiou et al. method of indicating the rate of re-perfusion utilizes plotted curves that indicate echo returns from interrogating ultrasound beams. Initially, Averkiou et al. transmit high energy ultrasound pulses to destroy the microbubbles in the region to be imaged. A short time later, lower energy, imaging, ultrasound pulses are transmitted again, the echoes received and imaged to measure the degree of microbubble re-infusion by, for example, counting or integrating the pixels in the area which show rein-fused microbubbles. The measure of the number of rein-fused microbubbles in the region is plotted in curve format. Non-destructive pulses can thereafter be repetitively transmitted and echoes received and plotted as a sequence of points to indicate the rate of re-perfusion.

U.S. Pat. No. 5,879,303 to Averkiou et al. discloses still another ultrasound method for imaging of contrast agents. In this patent, a programmable digital filter is used to pass harmonic echo components to the exclusion of fundamental frequency components of the transmitted signal. The system uses decorrelated replicas of the harmonic signal that are then combined and used for imaging. To produce an image in the presence of depth dependent attenuation of high frequency echo signals, both fundamental and harmonic signals are processed and used to produce an image blended from components of both the fundamental and harmonic signals.

U.S. Pat. No. 5,577,505 to Brock-Fisher et al. discloses an ultrasound method for imaging of contrast agents that achieves increased sensitivity to non-linear responses, particularly second harmonic responses under multiple excitation levels. In particular, the responses gathered from multiple echoes are gain corrected in an amount corresponding to the difference in excitation levels and are then subtracted. The subtraction removes most of the linear tissue response and what remains is the non-linear response from contrast agent.

It is known that the contrast ratio of ultrasound images is limited by a second harmonic response that results from interaction between tissue and incident ultrasound acoustic energy. Such harmonic response is caused by nonlinear propagation effects which give rise to second harmonic energy in the transmitted acoustic signal. Further, when contrast agent is destroyed, its acoustic response ceases to be constrained by frequency regions around the transmit frequency or harmonics thereof. More specifically, immediately after a microbubble contrast agent is destroyed, its acoustic response becomes broadband and exhibits energy in a broad spectrum of frequencies.

There is a need for improved ultrasound images from contrast agent. Further, harmonic tissue response in such images should be reduced to enhance the contrast of the contrast agent echo returns so as to improve images that are derived therefrom.

SUMMARY OF THE INVENTION

The method of the invention controls an ultrasound system to image a microbubble contrast agent in a region of fluid flow. A transducer is caused to transmit ultrasound signals and to receive echoes resulting from interaction of the ultrasound signals with both tissue and microbubbles. A transmitter enables the transducer to transmit the ultrasound signals at a plurality of power levels. A receiver selectively extracts signal components from the echo signals that fall within a determined bandwidth, and is controlled to alter the determined bandwidth (or the center frequency thereof) in accordance with the transmission's power level.

BRIEF DESCRIPTION OF THE DRAWINGS

FIG. 2 a plot of transmit signal frequency power and receive signal second harmonic bandwidth versus power, also showing the bandwidth of a receive filter function.

DETAILED DESCRIPTION OF THE PREFERRED EMBODIMENT

Figure 1:
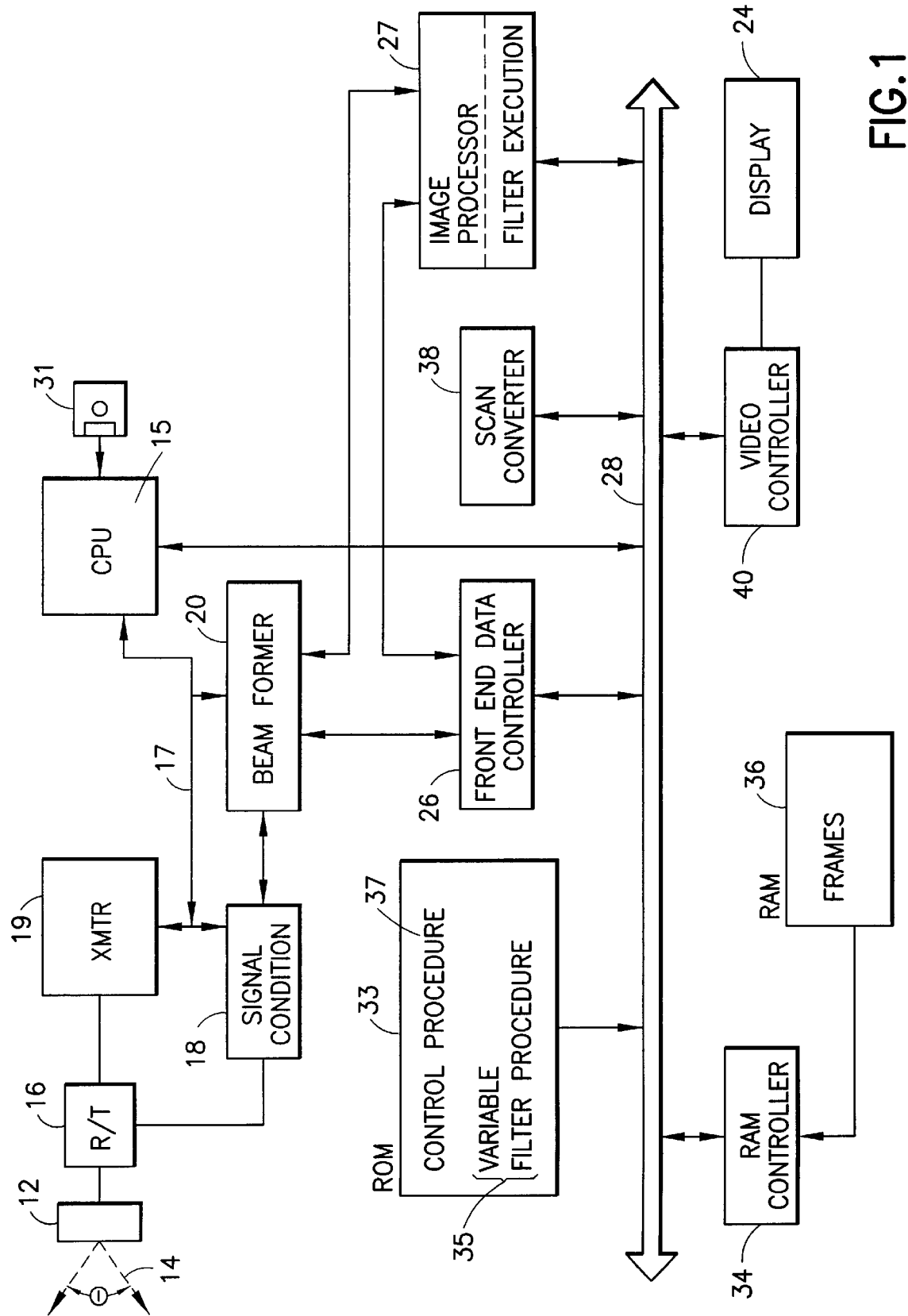
FIG. 1 is a high-level block diagram of an ultrasound imaging system incorporating the invention.

It is a fundamental characteristic of nonlinear physiologic ultrasound targets that their backscattered spectrums change as a function of incident acoustic pressure. For a system to develop maximum signal-to-noise or signal-to-clutter ratios, when imaging such nonlinear targets, it has been found to be desirable to vary the receive frequency characteristics of the ultrasound system in a manner that depends on the transmit power level.

Specifically, when a microencapsulated contrast agent is in use and the transmit power level is high, the contrast agent is destroyed by the incident acoustic pressure. When this occurs, the acoustic signal emitted by the rupturing microbubbles is of a much wider frequency bandwidth than when rupturing is not occurring, such as at lower incident acoustic pressures.

According to the preferred embodiment of the invention, the frequency bandpass characteristics of the ultrasound receive path are altered in accordance with the transmit power level. More specifically, as the transmit power level is adjusted by the user or by internal system control features, the central receive frequency, the receive bandwidth, or other receive frequency characteristics are adjusted automatically in response to the transmit power level setting.

During the following description of the invention, it will be assumed that ultrasound system 10 (see FIG. 1) has been adjusted so as to image an ROI within a patient's anatomy and that a contrast agent has been introduced into the blood stream. An ultrasound acoustic signal is then transmitted so as to insonicate the contrast agent within the ROI, or at least, within a portion of the ROI that is to be imaged. The ultrasound signal may be adjusted to have various power levels, at least one of which exhibits sufficient energy to destroy the contrast agent microbubbles.

The transmitter is controlled to output one of plural power levels to a transducer so as to interrogate the ROI with a selected level of ultrasound energy. At the same time, the receiver bandwidth, for example, is adjusted in accord with the transmitted power level. The echo signals from the ROI are then received and processed through a filter function that passes signals lying in the selected bandpass.

If the power level is adjusted to a high enough level to destroy the contrast agent, a relatively broadband echo signal results from the destruction event. Accordingly, the bandpass of the filter function is set to encompass the broadband response, preferably at the second harmonic of the fundamental frequency of the transmitted waveform. If the transmitted power level is less, i.e., not sufficient to destroy the contrast agent, the bandpass of the filter function is reduced so as to just encompass the frequency range of the expected second harmonic echo signals. In a similar manner, the center frequency of the bandpass of the filter function can be adjusted in accord with the expected echo signal characteristic Referring now to FIG. 1, ultrasound system 10 includes a transducer 12 that, in the known manner, scans an ultrasound beam 14 through a predetermined angle. A central processor unit (CPU) 15, via commands dispatched over line 17, controls the power of the signals that are output from transmitter 19 to transducer 12.

Concurrently, CPU 15 dispatches a command to image processor 27 to ready a filter function for execution. The specific filter function that is readied is dependent upon the transmit power of the signal output from transducer 12. Accordingly, image processor 27 calls variable filter procedure 35 from read only memory (ROM) 33 and readies it for execution by selecting a set of filter coefficients that will provide a desired filter bandwidth, center frequency, etc.

Radio frequency echo signals are sensed by transducer 12 and are fed through a receive/transmit switch 16 to a signal conditioner 18 and, in turn, to a beamformer 20. Signal conditioner 18 receives the echo signals and conditions those signals by amplification and forming circuitry, prior to their being fed to beamformer 20. Within beamformer 20 and under control of front end data controller 26, the RF acoustic signals are converted to coherent "lines" of digital RF signal values, in accordance with the echo signals from points along an azimuth of beam 14.

Beamformer 20 feeds the RF digital signal values to image processor 27 that buffers each line, as received. After one or more lines of digital values have been accumulated by image processor 27, front-end data controller 26 dispatches a signal that causes image processor 27 to commence execution of filter procedure 35.

With reference to FIG. 2, a plot of power versus frequency is shown that will enable a better understanding of the invention. Curves 100, 102, 104, and 106 represent succeedingly higher levels of transmit power versus bandwidth for transducer 12. Curves 100', 102', 104', and 106' represent the corresponding second harmonic echo signal magnitudes versus bandwidth that are received by transducer 12.

Each of curves 100', 102', 104', and 106' includes second harmonic returns from the microbubble contrast agent. Notice, that as the transmitted power increases, the resulting bandwidth of the echo signal increases (the bandwidth curves in the Figure are not drawn to scale). Further, at transmit power level 106, sufficient transmitted acoustic energy is present to destroy the microbubble contrast agent. Accordingly, echo return 106' exhibits a substantially broadened bandwidth (as a result of the contrast agent destruction).

When CPU 15 sets one of output power levels, 100, 102, 104 or 106, it concurrently instructs image processor 27 to select coefficients for variable filter procedure 35 that cause the filter action to exhibit a corresponding passband of 100", 102", 104" or 106". Thus the bandpass of the filter action is matched to the expected bandwidth of the echo signals, improving the selectivity and energy of the resulting passed signals. CPU 15 may also adjust the center frequency of the filter function or the shape of the bandpass characteristic, as desired.

Returning to FIG. 1, once all lines of a scan, at least within an ROI, have been processed by variable filter procedure 35, the resulting frame is stored in RAM 36, via RAM controller 34. A control procedure 37 then transfers the resulting frame to scan converter 38 where the data is converted to a raster image and is then passed to video controller 40 which causes the image to be shown on display 24. Accordingly. the resulting image is derived from signal energy that falls within the selected filter bandwidth and improved image contrast is the result.

It should be understood that the foregoing description is only illustrative of the invention. Various alternatives and modifications can be devised by those skilled in the art without departing from the invention. For example, while the procedures required to perform the method of the invention have been described as being already loaded into RAM or present in ROM, they may be stored on a memory device 31 (FIG. 1) and loaded on an as-needed basis. Accordingly, the present invention is intended to embrace all such alternatives, modifications and variances which fall within the scope of the appended claims.

What is claimed is:

1. An ultrasound system for imaging a microbubble contrast agent in a region of interest, said system comprising:

transducer means for transmitting ultrasound signals at a plurality of power levels and for receiving echoes resulting from interaction of said ultrasound signals with both tissue and said microbubble contrast agent;

receiver means for receiving said echoes and for selectively extracting signal components therefrom that fall within a determined bandwidth; and processor means for controlling said receiver means to alter said determined bandwidth in accordance with which of said power levels is transmitted.

2. The ultrasound system as recited in claim 1, wherein said processor means controls said receiver means to alter said determined bandwidth by decreasing said bandwidth at lower transmit power levels.

3. The ultrasound system as recited in claim 1, wherein said processor means controls said receiver means to alter said determined bandwidth by increasing said bandwidth at higher transmit power levels.

4. A method for controlling an ultrasound system to image a microbubble contrast agent in a region of interest, said method comprising the steps of:
  a) transmitting ultrasound signals at any of a plurality of power levels and receiving echoes resulting from interaction of said ultrasound signals with both tissue and said microbubble contrast agent;
  b) altering a determined receive bandwidth of said ultrasound system in accordance with which of said plurality of power levels is transmitted; and
  c) receiving said echoes and selectively extracting signal components therefrom that fall within said determined receive bandwidth.

5. The method as recited in claim 4, wherein step b) alters said determined receive bandwidth by decreasing said bandwidth at lower transmit power levels.

6. The method as recited in claim 4, wherein step b) alters said determined receive bandwidth by increasing said bandwidth at higher transmit power levels.

7. A memory media including instructions for controlling an ultrasound system to image a microbubble contrast agent in a region of interest, said memory media comprising:
  a) means for controlling said ultrasound system to transmit ultrasound signals at any of a plurality of power levels and to receive echoes resulting from interaction of said ultrasound signals with both tissue and said microbubble contrast agent;
  b) means for controlling said ultrasound system to alter a determined receive bandwidth of said ultrasound system in accordance with which of said plurality of power levels is transmitted; and
  c) means for controlling said ultrasound system to receive said echoes and to selectively extract signal components therefrom that fall within said determined receive bandwidth.

8. The memory media as recited in claim 7, wherein means b) controls said ultrasound system to alter said determined receive bandwidth by decreasing said bandwidth at lower transmit power levels.

9. The memory media as recited in claim 7, wherein means b) controls said ultrasound system to alter said determined receive bandwidth by increasing said bandwidth at higher transmit power levels.

10. An ultrasound system for imaging a microbubble contrast agent in a region of interest, said system comprising:
  a transducer that transmits ultrasound signals at a plurality of power levels and receives echoes resulting from interaction of said ultrasound signals with both tissue and said microbubble contrast agent;
  an image processor that selectively extracts, from the echoes, signal components that fall within a determined bandwidth; and
  a processor that alters said determined bandwidth in accordance with a power level of the ultrasound signals transmitted by the transducer.

* * * * *